United States Patent [19]
Pol et al.

[11] Patent Number: 4,576,606
[45] Date of Patent: Mar. 18, 1986

[54] IMPLANTABLE BLOOD PUMP

[75] Inventors: Vincent Pol, Marseille; Jean-Claude Dumas, Auriol, both of France

[73] Assignee: Clinique de la Residence du Parc, Marseille, France

[21] Appl. No.: 684,348

[22] Filed: Dec. 19, 1984

[30] Foreign Application Priority Data

Dec. 28, 1983 [FR] France ............................. 83 20933

[51] Int. Cl.⁴ ............................................. A61F 2/22
[52] U.S. Cl. ........................................ 623/3; 417/412
[58] Field of Search ..................... 417/412, 413; 3/1.7

[56] References Cited

U.S. PATENT DOCUMENTS

| | | | |
|---|---|---|---|
| 3,328,255 | 6/1967 | Ilg et al. | 424/101 |
| 3,513,486 | 5/1970 | de Bennetot et al. | 3/1 |
| 4,008,710 | 2/1977 | Chmiel | 128/1 D |
| 4,167,046 | 9/1979 | Postner et al. | 417/412 |
| 4,222,127 | 9/1980 | Donachy et al. | 3/1.7 |

FOREIGN PATENT DOCUMENTS

2102504 2/1983 United Kingdom .................... 43/12

Primary Examiner—Richard J. Apley
Assistant Examiner—James Prizant
Attorney, Agent, or Firm—Blakely, Sokoloff, Taylor & Zafman

[57] ABSTRACT

Inside a flexible shell (10), a deformable pocket (20) is connected to blood circulation via an inlet valve (30) and an outlet valve (40). The pocket is compressed by a floating assembly comprising a drum (50), and a bracket (60) rotatable about the axis thereof. One of the edges (21) of the pocket (20) is fixed to the drum (50); the opposite edge (22) is connected to the bracket (60) by a traction link (70), for example an inextensible sheet. Relative rotation between the drum and the bracket over a fraction of a turn enables the pocket (20) to be wrapped around the drum (50) and the assembly returns to its starting position under the effect of venous pressure. The disposition of the various components provides a self-adapting lever which limits mechanical losses to rolling friction between the drum and the pocket.

10 Claims, 12 Drawing Figures

FIG_5

FIG_6

FIG_7

FIG_11

FIG_12

IMPLANTABLE BLOOD PUMP

The present invention relates to an implantable blood pump.

The blood pump described herein is principally intended to provide ventricular assistance, for example to temporarily or definitively remedy failure of the left ventricle. However, the teaching of the invention may equally well be applied to a total heart prosthesis, by providing two associated ventricles each provided with its own valves.

BACKGROUND OF THE INVENTION

Numerous devices have been proposed for constituting a heart ventricle prosthesis. They are generally peristaltic-type pumps, i.e. they include a deformable pocket connected to the blood circulation path via an inlet valve and an outlet valve. The pocket is compressed by applying an external force thereto, generally by means of a pneumatic device under the control of a source of pressure.

From the physiological point of view, this type of pump behaves similarly to the natural heart (which is a contractile pocket), thereby obtaining the essential advantage of practically eliminating the phenomenon of hemolysis (i.e. the destraction of red globules), by considerbaly reducing phenomena of shock, turbulence, abrupt pressure variation, . . . in the blood fluid. The pocket is deformed by externally applied stress. It thus contains no internal moving member such as a piston in direct contact with the blood.

Another advantage of peristaltic pumps is that they always operate with blood admission at zero or slightly negative pressure. This thus avoids any risk of collapsus in the event of insufficient venous return. Such risks are capable of causing a pump to operate wrongly and to cause the patient to die quickly by crushing the auricular cavity and/or the vessels, and they are inherent to displacement-type pumps which therefore require either to control the flow-rate very accurately to the blood pressure, or else they require a buffer volume, which can only be provided outside the body because of the resulting extra bulk.

However, in prior proposals, pneumatic drive is an obstacle to providing a prosthesis which is completely implantable and autonomous. Firstly, the pneumatic device is voluminous (a source of pressure, electrically controlled valves, and a pneumatic regulator device) thus requiring apparatus outside the patient and connected to the patient by pneumatic links.

Then, and most particularly, the overall efficiency of a pneumatic compressor is low, thus requiring a high power source of electrical energy. Such sources are heavy and voluminous, and above all because of the low efficiency of the electro-pneumatic conversion, they generate large quantities of heat which is incompatible with the human body's thermoregulation system.

Finally, a pneumatically driven heart uses thin diaphragms (for transforming the pneumatic energy supplied into mechanical pumping energy), which are particularly exposed to the risk of rupture, in particular following spots of calcification which weaken the diaphragm wall.

Preferred implementations of the present invention provide a heart pump which mitigates these drawbacks.

The pump in accordance with the invention is of the peristaltic type, thereby benefitting from the advantages related to the absence of a moving member inside the pocket (and thus a very low degree of hemolysis), and to non-displacement operation (thereby avoiding the risk of venous collapse).

One of the aims of the present invention is to provide an entirely implantable and autonomous prosthesis for a ventricle or a heart. Because of the excellent efficiency of an assembly for converting electrical energy into mechanical pumping energy, it is possible to limit the energy consumption of an electrically driven prosthesis to values which are compatible with small sources of electricity (batteries or isotope cells) which could be implanted, or which could at any rate be conveniently carried by the patient in such a manner as to enable the patient to move about freely.

The excellent efficiency also makes it possible to limit the heat dissipation to values which are compatible with natural thermoregulation. It is shown that the total power consumed by the pump (developed mechanical power+heat losses) is of the same order of magnitude as the theoretical physiological power of a natural heart.

Further, the disposition of the various components constituting a pump in accordance with the invention make it possible, without reducing performance, to provide a pump having an overall shape and size similar to those of a natural organ. This compact disposition facilitates the implantation of one or two artificial organs.

It is also shown that the pump has a degree of flexibility enabling it to absorb the movements of the thorax (breathing, coughing) in the same manner as a natural heart. This avoids certain difficulties which are encountered when a rigid organ is implanted, as has been the case in certain prior art proposals.

Finally, it will be shown that in addition to the possibility of servocontrolling the pump regime (flowrate, frequency, waveform) to blood pressure, the very structure of the pump provides automatic adaptation. In other words, if the blood pressure increases the volume of the ventricle tends to increase due to elastic deformation. Under such conditions, and without any change in the heart frequency nor in the form of the pressure wave, the volume output at each contraction increases, thereby improving the irrigation of the patient. In this case, the prosthesis has higher performance than the natural organ since the natural tissues do not allow the ventricle to dilate under the effect of an increase in blood pressure.

SUMMARY OF THE INVENTION

These various aims are achieved, according to the invention, by a pump which comprises:

an outer shell which is advantageously deformable as a whole;

at least one closed elastically deformable pocket which is fed with blood fluid via an inlet valve and which is capable of ejecting said fluid via an outlet valve;

said pocket being substantially flat when unstressed and being placed against the inside wall of the shell in such a manner as to present two walls, which, following the curve of the shell both have their concave sides directed towards the interior of the shell, these two walls extending between two longitudinal elongate regions forming proximal and distal ends;

a drum, with the proximal end of the pocket connected to the periphery thereof;

a bracket rotatably mounted on the longitudinal axis of the drum;

means for providing a traction link between the bracket and the distal end of the pocket; and means for driving the bracket and the drum in mutual antagonistic rotation over a fraction of a turn in a direction enabling the drum to come into rolling contact with the wall of the pocket while the bracket holds the distal end and tends to bring it closer to the drum.

In this manner, the pocket is compressed under the effect of its being wrapped around the drum while ensuring that the successive positions of the drum-bracket assembly follow a movement of least resistance between the compression reaction of the pocket and the traction reaction of the distal end of the pocket.

By chosing to use a deforming closed pocket as the pumping volume, it is possible to retain the advantages procured by peristaltic operation as explained above. Further, this pocket has a structure which may be considered as a virtual physiological cavity (or more precisely a semi-virtual cavity): such a cavity is a cavity which, when empty, occupies practically no volume, with its inside walls coming into contact with each other. Thus, because of its flat shape when unstressed, the pocket used in the invention forms a cavity which practically ceases to exist at rest (i.e. in the absence of any blood pressure). In fact, it is preferable to leave a very thin layer of liquid inside the pocket (1 to 1.5 mm thick) in order to limit the risk of hemolysis phenomena appearing; that is why this pocket defines a "quasi virtual" cavity.

The main function of the shell is to constitute a bearing surface during at least part of the pump stroke; in particular on starting when a pocket full of blood tends to be pushed away from the drum which is compressing it. Keeping the pocket pressed against the shell after starting provides, in addition, excellent evacuation of the pocket since it is deformed between the drum and the shell.

Preferably, a link is provided between the bracket and the outer shell, said link being a loose link enabling the bracket to pivot relative to the shell, at least about a longitudinal axis.

Preferably, the material consititating the shell is a material having its own geometrical memory. This improves energy restitution: the material's own memory is added to the deformation due to the relative displacement of the drum and the bracket.

This enables the shell to perform a second function as an elastic energy store, thereby improving the operation of the pump both as to quality (an improved pressure wave shape) and as to quantity (improved overall efficiency, improved ejection pressure). The elastic energy due to deformation of the pocket is returned to the system at the moment of starting, i.e. at the moment when the energy is most useful for assisting the motor since the motor is short-circuited at the beginning of pocket compression. This effect of restitution of elastic energy by the shell is comparable to the restitution of energy by the cardiac fibers of a natural heart.

Advantageously, the means for providing a traction link between the bracket and the distal end of the pocket include an inextensible sheet connecting these two items over their entire length. This makes the traction effect uniform over the entire height of the pocket and avoids the bracket being moved off axis. The axis of the bracket should move parallel to itself to avoid any sliding of the drum over a pocket.

The drive means advantageously include an electric motor whose outer stator body is fixed to the drum and whose rotor drives the bracket via a stepdown gear (for a normal motor) or without a stepdown gear (for a torque motor), together with means for determining the relative angular position of the bracket relative to the drum and cooperating with means for interrupting the power supply to the drive means when a predetermined angular value has been reached.

The electric motor is then preferably a reversible motor which is powered with reversed voltage at reduced value once the predetermined angular value has been reached to assist the return of the pump components to their starting position. A free, unassisted, return would also be possible, simply under the effect of the filling pressure (venous pressure) and of the elasticity of the pocket, however, such a return would be too long to correspond to a normal cardiac rhythm. In addition, the return period would be subjected to the influence of numerous difficulty-mastered parameters. That is why it is preferred to control the return to the starting position, and thus the filling period.

In this case, the reverse voltage at reduced value may be a variable voltage in such a manner as to adjust the duration of the return phase as a function of a signal setting the operating frequency. This signal may, for example, be a physiological signal supplied by the right heart (where left ventricle assistance is being provided), or it may be a signal obtained from an auricle retained for the purpose, or it may be a non-physiological predetermined frequency.

If a complete heart prosthesis is envisaged, a pump in accordance with the invention may include two closed pockets, each having its own inlet valve and outlet valve with the two pockets being adjacent inside the shell and having their respective proximal ends connected together with the drum and their respective distal ends connected together with the bracket via a common traction link.

In particular, the left ventricle may be in direct contact with the drum while the right ventricle is only compressed indirectly by the left ventricle and not by the drum.

Such operation approaches the operating conditions of the natural heart in which the left ventricle supplies substantially all the pumping energy of the heart; it also provides proper synchronization between the two ventricles.

BRIEF DESCRIPTION OF THE DRAWINGS

Embodiments of the invention are shown by way of example with reference to the accompanying drawings, in which.

MORE DETAILED DESCRIPTION

Figure 1:
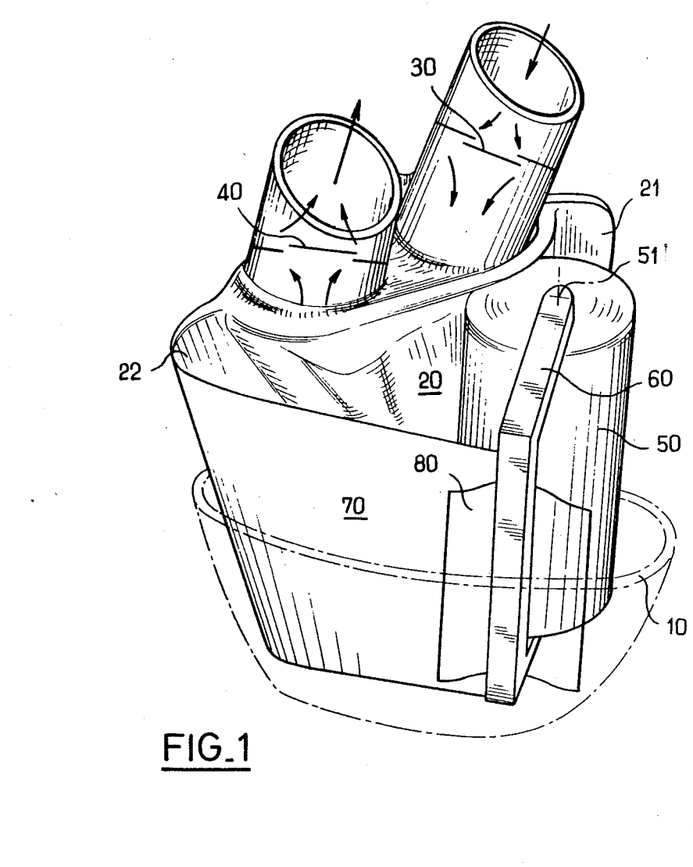
FIGS. 1 to 3 are partially cut-away views of a pump in accordance with the invention, and respectively comprise a perspective view, a front view, and a side view.
Figure 2:
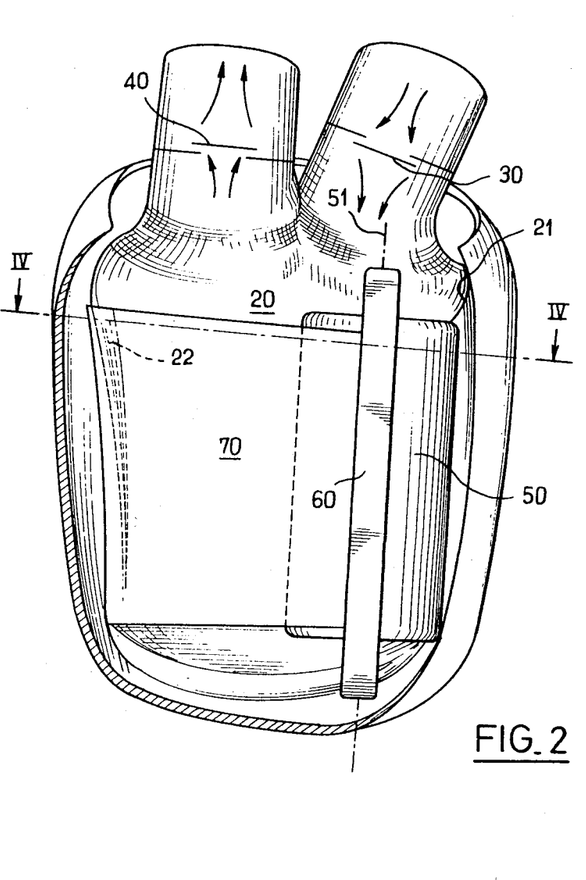
Figure 3:
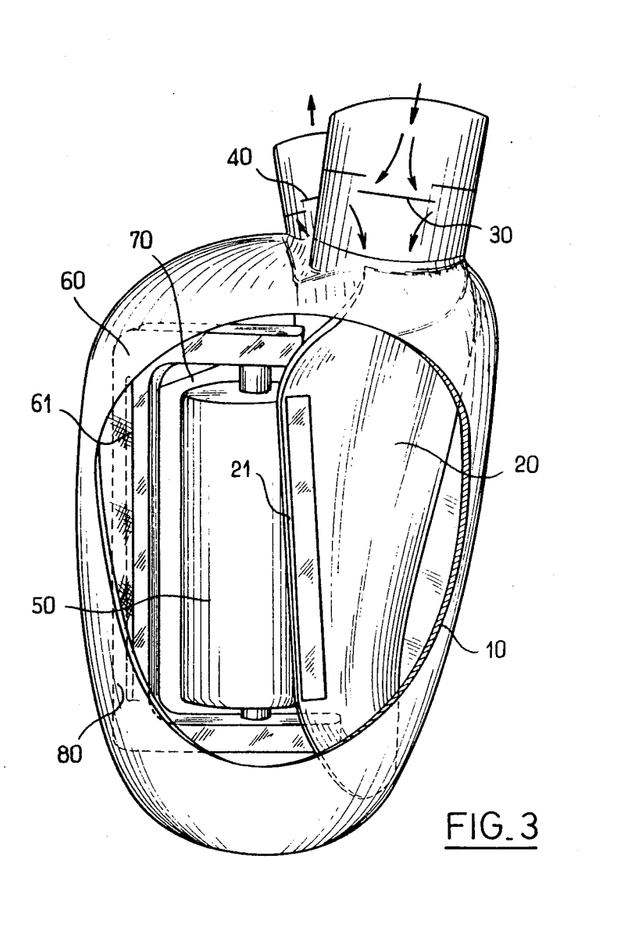

In FIGS. 1 to 4, the pump assembly can be seen situated inside a shell 10 which constitutes an outer envelope and which is shown partially cut away in FIGS. 1 to 3. A pocket 20 whose unstressed shape is flat extends between two end regions 21 and 22. In the cross-section of FIG. 4, the pocket is generally crescent shaped and the degree to which it is flattened depends on the pressure of the filling liquid. In particular, in FIG. 4, the continuous line shows the profile of the pocket when empty, while the dashed line shows the shape of the pocket when full at a pressure of 50 mmHg (6600 Pa) for example, in which case its capacity is about 75 cm$^3$.

This pocket is supplied with blood fluid via an inlet valve 30 of conventional type (e.g. a rocking disk); since it is filled without aspiration, the inlet valve must open for a pressure difference of about 10 to 12 mm Hg (1300 to 1600 Pa).

When compressed, the pocket 20 ejects the blood fluid via an outlet valve 40 which may likewise be of conventional type, but which must be capable of withstanding a back pressure of at least 140 mm Hg (19000 Pa). This value corresponds to the maximum arterial pressure for a subject having a healthy arterial network. It may vary depending on the strength of the peripheral vessels, particularly in the event of atherosclerosis.

The proximal end 21 of the pocket is fixed to a drum 50 which is articulated on a bracket 60 about an axis 51. The other or distal end 22 of the pocket is connected to the bracket 60 by an inextensible sheet 70.

In addition, and advantageously, the bracket 60 is connected to the shell 10 by means of a link 80. This link is not a rigid link. It merely defines a zone in which the bracket may move relative to the shell and it enables at least the vertical portion of the bracket to pivot about a longitudinal axis. This link may be provided, as shown, by means of a sheet of synthetic cloth which is glued or sown to the shell 10 and which passes through a slot 61 (FIG. 3) in the middle portion of the bracket. Such a link over a large portion of the length of the bracket ensures good uniformity in the coupling between the shell and the bracket.

However, such a link between the shell and the bracket is not essential for the combination of means proposed by the present invention. This combination is directed to an intrinsically "floating" connection, i.e. one capable of operating without an external bearing point (in the same manner as a natural contractile pocket).

If there is no link between the shell and the bracket, the shell does not have a mechanical role and is merely provided as a protective unit.

Indeed, this variant may be preferred in some cases, in particular when the implanted organ is liable to be subjected to external stresses (e.g. thorax compression) which could affect its proper operation. In such a case, the shell is reinforced (e.g. by means of a grid of metal reinforcing wires to reinforce its protective role). If a too-flexible shell is compressed there could be an unfortunate limitation of the operating stroke of the device. To avoid erratic movement of the device inside a shell made rigid in this manner, the outside wall 24 (FIG. 4) of the pocket could be fixed to the shell, e.g. by a spot of glue. This connection between the shell and the pocket has no operational role coupling the two components. Its only use is to limit relative movements during operation.

The shell is made of a biocompatible material such as a silicone rubber or a polyurethane which makes it possible to associate a geometrically deformable shape of the shell with a material possessing its own memory. If such elasticity is not required, the material may be reinforced by means of a synthetic copolymerized cloth.

The pocket 20 is also made of an elastically deformable biocompatible material, e.g. a silicone rubber such as Silastic (registered trade-mark). This material, when in contact with blood, is known for its low risk of thrombo-embolism accidents, provided that its surface condition is extremely carefully prepared, which may require moulding on highly-polished surfaces, for example. The thickness of the pocket should be about 1 to 2 mm, thereby making it unbreakable even if it has points of calcification thereon.

In the example shown (particularly in FIGS. 3 and 4) the pocket is formed by two superposed plane sheets which are welded together at their peripheries and also to the valves 30 and 40. When placed in the shell, these sheets are curved (which curvature is accentuated by the tension from the sheet 70), thereby giving them the shape shown in the second of FIG. 4 which corresponds, when empty, to a "semi-virtual cavity" as explained above. The end zones 21 and 22 are not necessarily parallel edges nor need they be rectilinear. In the example shown, the two sheets constituting the pocket are substantially trapezoidal in shape, with the edges 21 and 22 forming nonparallel sides. However, other shapes may be envisaged as a function of numerous parameters such as the capacity of the pocket, the shape of the drum 50, a search for a more easily implantable shape, etc. In addition, the shape of the pocket is chosen to enable ejection with low overall deformation (as will be seen on examining FIGS. 4 to 10), without the material being folded and with small relative displacement of the valves 30 and 40 which should be subject to minimal stress by the pocket to which they are connected.

It is also possible to envisage moulding the pocket 20 as a single piece, which would avoid having to connect two parts along its extreme zones 21 and 22.

The drum 50 has been shown as a right circular cylinder rotating about its axis. However, numerous variants could be envisaged, e.g. a circular cylinder could rotate about an axis excentric to its own axis, or the cylinder could be formed by generator lines other than rectilinear lines; or the cylinder need not have circular symmetry.

The drum could be constituted by a fraction of a circularly symmetrical cylinder (since only a portion of the cylindrical surface actually makes contact with the pocket), or it could be any other suitable shape.

The shape of the drum depends on its position relative to the valves (the upper portion of the cylinder must deform them very little), on the volume and on the shape of the pocket (to avoid dead volumes), and on the compression force rising progressively. Likewise, the axis 51 of rotation may be inclined (see FIG. 2) relative to the vertical to provide improved evacuation of the pocket towards the outlet valve.

In all cases, the essential function of the drum is to cooperate with the pocket to wrap the pocket round the periphery of the drum without relative sliding between the surfaces. The resulting compression of the pocket will always be with minimum friction, since rolling friction coefficients are always very low in the absence of sliding.

The traction link 70 is connected by an inextensible sheet of synthetic material, e.g. silicone. This link extends over the entire length of the central portion of the bracket and enables the bracket to urge the drum towards the end 22 of the pocket while guiding the drum so that it rolls over the pocket without sliding.

The motor used for driving the bracket relative to the drum over a fraction of a turn may, in a first embodiment, be a torque motor associated with a stepdown gear (so as to have a large torque available at the end of a shaft). In which case, it is important to avoid any angular drift which would progressively bring the drum into abutment with the shell. To reset the assembly after each fraction of turn, a magnetic sensor 90 disposed on the bracket (see FIG. 5) may be used to detect the presence of magnets 91, 92 mounted on the drum and corresponding to the allowable extreme positions.

The maximum angle of rotation is about 100° in the example shown, but this value depends to a large extent on the motor-shell-pocket geometry.

In a second embodiment, it is possible to use a brushless motor controlled by a train of pulses, thereby avoiding the need to use an angular position detector, with relative displacement of stator and the rotor being proportional to the number of pulses sent.

However, in such an embodiment, a subsidiary angle position detector could nonetheless be provided for safety reasons, thereby backing up the pulse count.

Another safety measure may be constituted by an overcurrent detector, for turning off the power supply to the motor if it does not reach its extreme angular position. This safety measure will nevertheless enable the device to continue operating.

The motor itself is selected from high efficiency miniaturized models, e.g. those using samarium-cobalt magnets. The problem of motor efficiency is particularly acute in this application, insofar as the operation is intermittent rather than continuous rotation. The energy needs of a motor are highest on starting, i.e. when the motor is a short-circuit and thus when its instantaneous efficiency is lowest.

The power supply to the motor (not shown) may be in the form of implanted rechargeable batteries, or external batteries with a percutaneous passage, or preferably with a transcutaneous passage (i.e. electromagnetic coupling).

Further, the excellent efficiency of a pump in accordance with the invention makes it possible to envisage implanting an isotope cell. Although such a generator of electricity is itself a low efficiency device, the power which it delivers is sufficient for powering a pump in accordance with the invention, since the required power is close to the theoretical physiological power (i.e. a few watts). Dissipating the heat generated by such a low-power cell, remains compatible with natural thermoregulation.

The dynamics of a pump in accordance with the invention are now described with reference to FIGS. 4 to 10.

Figure 4:
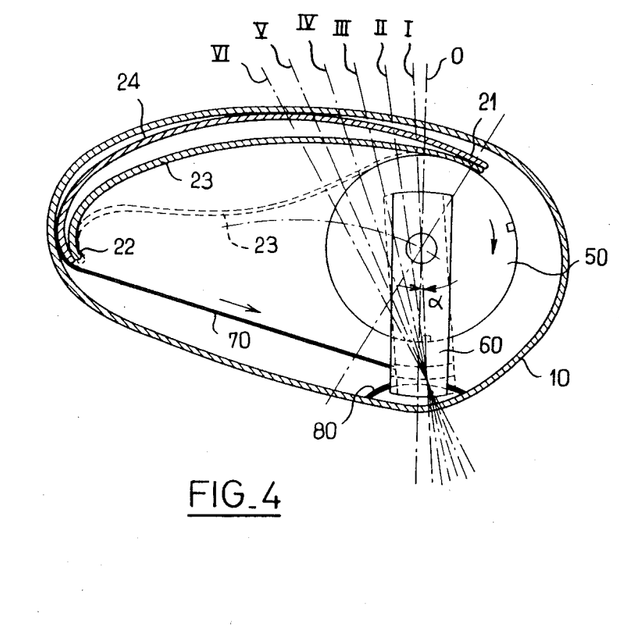
FIG. 4 is a diagrammatic section on a line IV—IV in FIG. 2.
Figure 5:
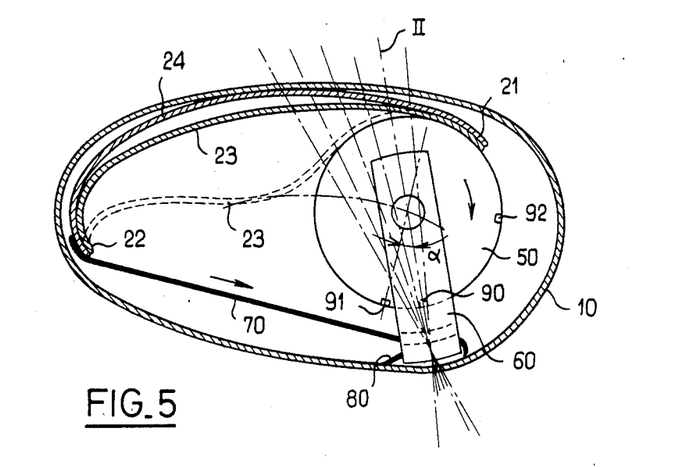
FIGS. 5 to 10 show the operating dynamics of the invention.
Figure 6:
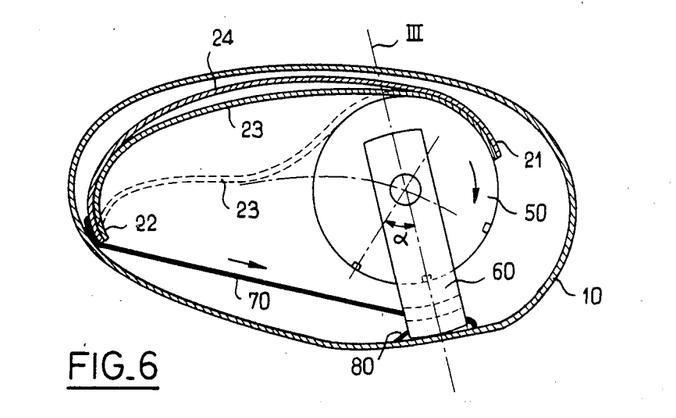
Figure 7:
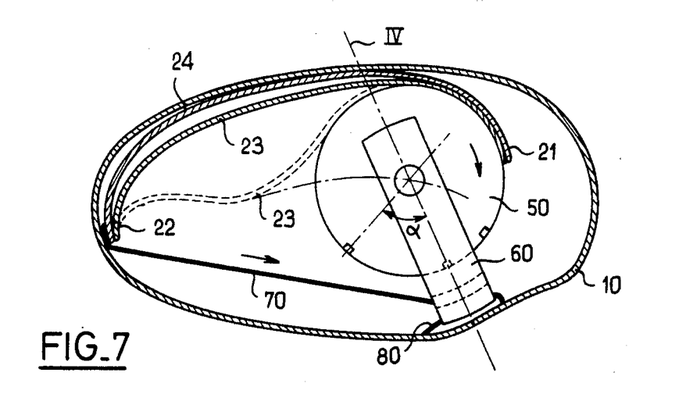
Figures 8, 9:
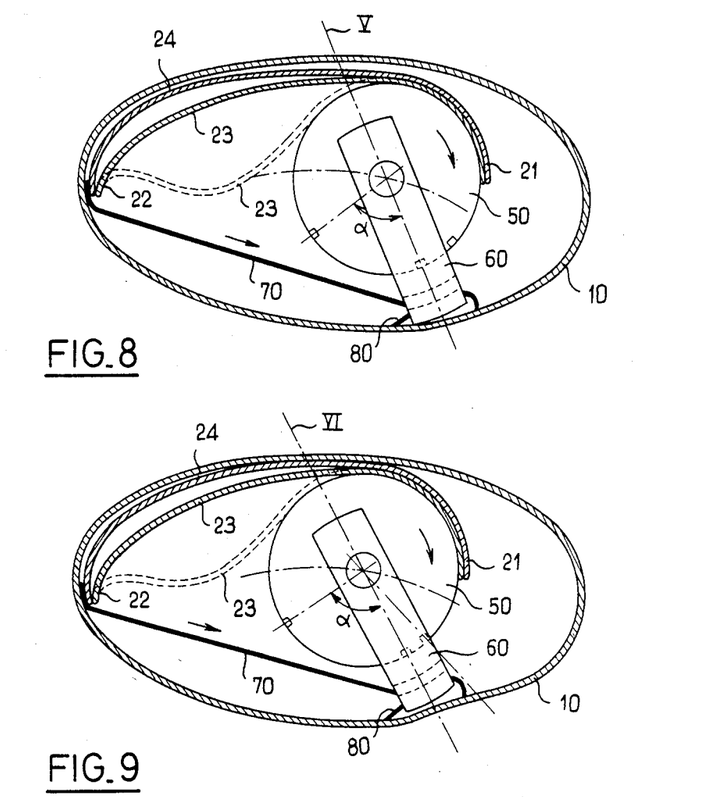
Figure 10:
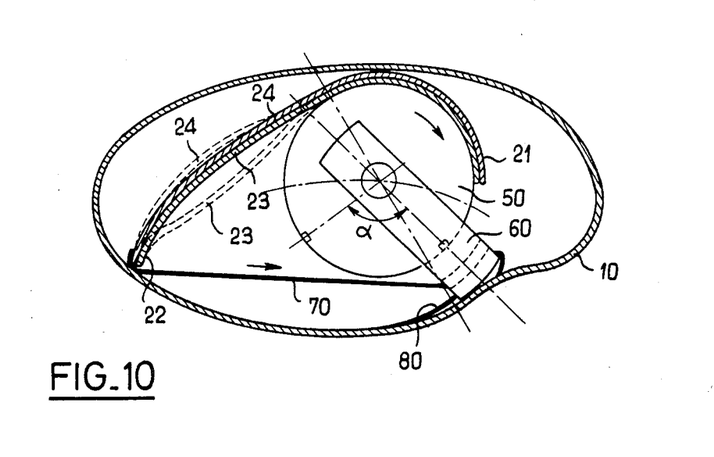

In FIG. 4, a certain number of positions designated O, I, . . . VI are shown, and the bracket positions II to VI correspond to FIGS. 5 to 9.

In position O, the pocket 20 is full of blood fluid (profile shown in dashed line in the figures), and the drum 50 hardly bears against the pocket at all; at the same time, the sheet 70 is slack.

When the motor starts, the drum will bear against the wall 23 of the pocket, thereby causing a reaction in which the bracket moves from position O to position I, thus putting the sheet 70 under tension. The pocket 20 then abuts against the inside face of the shell 10, thus creating a bearing point (at least during start-up). Thereafter, the drum and the bracket follow a movement of least resistance, thus automatically matching the compression reaction on the pocket by the drum and the traction reaction via the sheet.

In particular if the pocket offers high resistance to compression by the rolling drum 50, the drum tends to stay put causing most of the displacement (absolute displacement) to be performed by the bracket 60. This displacement of the bracket increases the tension on the sheet 70 until this tension is in equilibrium with the reaction of the pocket to compression. This period during which the resistance to compression is high occurs, for example, at the very beginning of ejection (positions O and I of FIG. 4, where the sheet is under low tension), or else at the end of ejection (FIGS. 9 and 10) or else if the blood pressure is high.

In contrast, if the compression resistance provided by the pocket is relatively low, the drum 50 tends to roll over the pocket and to deform it and to wrap it round the periphery of the drum; in this case the bracket serves merely as a shaft support. This situation corresponds to FIGS. 5 to 8 (in which it can be seen that the length of pocket wrapped round the drum increases rapidly), or else to a case of low blood pressure.

Such a "floating" assembly of the system provides a permanent inversion about an equilibrium position of the bearing point and the point of application of the force exerted by the drum-bracket assembly which constitutes an articulated lever. Either the drum bearing against the pocket serves as a bearing point for the bracket so that it can exert traction on the distal end of the pocket and thus draw said end towards the drum; or else the bracket is held in place by the traction exerted by the sheet 70 and serves as a support for the drum which rotates and winds the pocket round its periphery.

Likewise, when the pocket comes into contact with the shell, friction at the point of contact tends to immobilize the pocket. As a reaction, the drum starts to wind in the pocket, and the resultant winding will bring the pocket inwardly thus reducing its contact with the shell and the friction at that point.

In any event, the assembly "runs away from friction", i.e. deforms itself so that the drum is in the position which ensures minimum friction which is essentially a very low value of rolling friction.

This self-adapting or self-matching system explains the excellent performance of the device, in praticular its high efficiency at transforming electrical energy into pneumatic pumping energy.

It may also be noted that the absolute displacement of the drum is very small (either by direct winding or else by drawing th distal end towards the drum) unlike conventional peristaltic pumps used outside the body, where the deformable cavity remains immobile.

The total duration of the ejection phase (systole) is about 350 ms—corresponding to the sequence of FIGS. 4 to 10—; at the end of ejection, it is advantageous to leave a layer of blood which is about 1 to 2 mm thick (see FIG. 10) between the two walls of the pocket to avoid any risk of hemolysis.

The filling phase (diastole) takes place by the assembly returning to its initial position. As mentioned above, this return results from venous pressure, the pocket's own elasticity, energy restituted subsequent to deformation of the shell, and also to reverse voltage applied to the motor to assist the return phase.

Advantageously, the duration of the return phase may be modified while conserving a constant duration for the ejection phase. Thus, the total duration may be variable and may, for example, be servo controlled to a reference heart rate signal.

The energy supplied by the motor during the return phase is very low, about 1/100th of the energy needed during the ejection phase; this energy is required simply to accompany the movement of the pocket which unwinds from the drum under a natural filling effect due to venous pressure. It may be observed that the distribution of energy as a function of time is comparable to the physiological function of a natural heart in which the energy developed is practically nil for ⅔ of the cardiac period.

Figure 11:
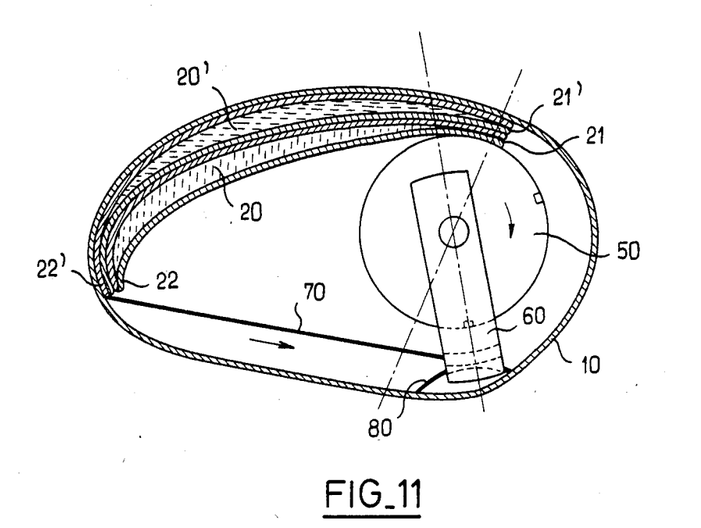
FIG. 11 is a section, similar to FIG. 4, but corresponding to a total prosthesis, i.e. for assisting both ventricles.

FIG. 11 shows an embodiment in which two superposed pockets 20, 20' are provided rather than just one pocket, each of the pockets having its own valves (not shown) and the device thus being suitable for constituting both ventricles of an implantable total prosthesis.

The two pockets are superposed inside the same shell 10. Their proximal ends 21, 21' are connected together to the drum 50 while their distal ends 22, 22' are connected together to the bracket 60 by a single sheet 70. (The adjacent internal walls of the two pockets 20, 20' could, naturally, be constituted by a single partition wall).

In this manner, movement of the drum and of the bracket produces simultaneous and substantially synchronous compression in both pockets 20, 20'. The pocket 20 (the innermost pocket) is directly compressed by contact with the drum. The other pocket 20' is only indirectly compressed because of the interposition of the first pocket 20 between the outer pocket and the surface of the drum. The compression force is thus less in the second pocket and it delivers a lower pumping power and a lower ejection pressure.

Advantage may be drawn from this feature by providing for the pocket 20 to constitute the left ventricle of the prosthesis while the pocket 20' constitutes the right ventricle. The difference in pumping power and in pumping pressure between the two pockets then corresponds to a physiological state of affairs: the right ventricle only provides circulation through the lungs, and therefore provides much less force than the left ventricle which serves to ensure the entire peripheral circulation.

Figure 12:
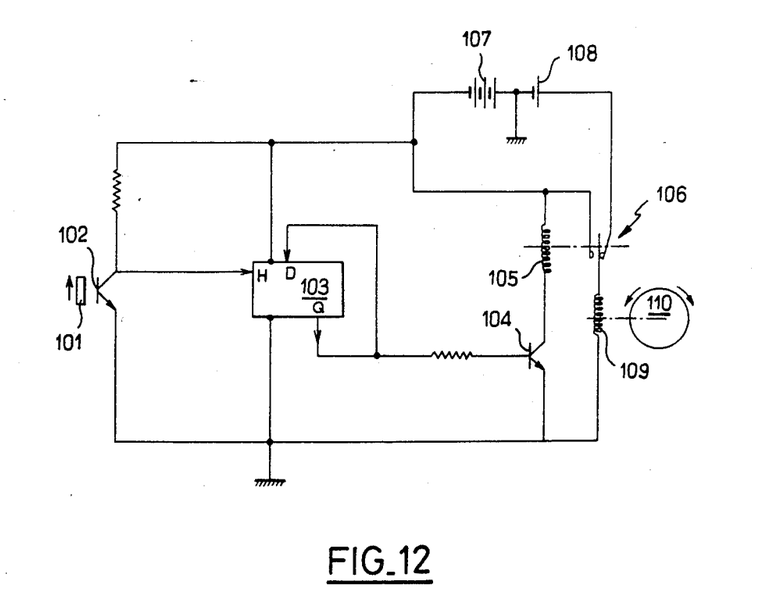
FIG. 12 is a circuit diagram of an example of a control circuit for the motor of a pump in accordance with the invention.

FIG. 12 is a diagram of an electronic circuit suitable for controlling the operation of the above-described pump, regardless of whether it is a one-ventricle or a two-ventricle model.

A permanent magnet 101 (alternating between the two magnets 91 and 92 shown in FIG. 5) passes in front of a detector 102, e.g. a Hall effect detector, each time one of the extreme positions is reached. To reverse the direction of motor rotation at that moment, a D-type bistable 103 has its clock input H excited by the voltage variation at the terminals of the detector 102. Its Q output is fed back to its D input and also serves to drive a transistor 104 for controlling the winding 105 of a reversing relay. The contacts 106 of this relay alternately switch the winding 109 of the motor 110 to two voltage sources 107, 108 of opposite polarity (since the source 108 corresponds to the return phase, it is advantageously a lower voltage source than the source 107).

Thus, the circuit 103 and the relay 105 switch over causing the motor direction to be reversed each time an extreme position is reached as detected by the passage of one or other of the magnets past the detector 102. Naturally, the electromechanical relay with a winding and contacts as shown may be replaced by a purely static relay having a semiconductor junction.

EXPERIMENTAL RESULTS

In vivo experiments with a left ventricle assisting pump as described above (in the variant with a reinforced shell and in the absence of any coupling between the shell and the bracket) has been performed on pigs. The cardiovascular and respiratory physiological constants of this animal model are close to those of man and animals of much the same weight may be selected.

Surgically, the implant was performed without using circulation outside the body, by lateral clamping of the aorta and of the left auricle. This operational simplification (which will not be used on man) makes the operations of purging and starting the prosthesis much more difficult.

In spite of this difficulty, the operations took place without incident on the five animals implanted.

In each experiment, successive tests were performed either by clamping the descending aorta, with the artificial ventricle then feeding the entire lower portion of the animal, or else by total aorta clamping, with the left ventricle providing the entire left cardiac function except for the coronaries which remained supplied by the natural heart.

During these clamping operations which enabled the left ventricle to pass from an assistance function to a replacement function, automatic and immediate adaptation of the prosthesis to the different pressure and flow-rate conditions was observed.

This result which is unique when compared with other prosthesis is essentially due to the absence of aspiration by the artificial ventricle. Further, the variable filling rate of the left ventricle which depends only on the venous return to the left auricle does not modify the ejection pressure which varies according to need between 80 and 140 mm of mercury (11000 and 19000 Pa). This variable filling rate confirms the non-suction operation, and thus non-displacement operation of the pump, thereby avoiding any risk of collapsus.

After 10 hours of implantation, regularly performed analysis showed no destruction of red globules (hemolysis) nor any platelet aggregation. This result is likewise of great importance.

All biological analyses remained normal.

In parallel, inert or ghost prostheses were implanted to verify compatibility of the materials used with the biological organism. So far, one month after implantation, no abnormal reaction has been observed.

The voltage and current curves of the left ventricle in operation as obtained by an automatic tracing device, have made it possible to calculate that the average consumption of the pump is about 2.25 watts for a flow-rate of 50 $cm^3$ per systole at a pressure of 140 mm of mercury.

We claim:

1. A blood pump, comprising:
   an outer shell;
   at least one closed elastically deformable pocket which is fed with blood fluid via an inlet valve and which is capable of ejecting said fluid via an outlet valve;

said pocket being substantially flat when unstressed and being placed against the inside wall of the shell in such a manner as to present two walls, which, following the curve of the shell both have their concave sides directed towards the interior of the shell, these two walls extending between two longitudinal elongate regions forming proximal and distal ends;

a drum, with the proximal end of the pocket connected to the periphery thereof;

a bracket rotatably mounted on the longitudinal axis of the drum;

means for providing a traction link between the bracket and the distal end of the pocket; and means for driving the bracket and the drum in mutual antagonistic rotation over a fraction of a turn in a direction enabling the drum to come into rolling contact with the wall of the pocket while the bracket maintains the distal end and tends to bring it closer to the drum;

in such a manner as to enable the pocket to be compressed under the effect of its being wound around the drum; and in such a manner that the successive positions of the drum-bracket assembly follow a movement of least resistance between the compression reaction of the pocket and the traction reaction of the distal end of the pocket.

2. A blood pump according to claim 1, further provided with a link between the bracket and the outer shell, said link being a slack link enabling the bracket to pivot relative to the shell, at least about a longitudinal axis.

3. A blood pump according to claim 1, wherein the outer shell is geometrically deformable overall.

4. A blood pump according to claim 3, wherein the shell is made of a deformable material having its own memory.

5. A blood pump according to claim 1, wherein the means for providing a traction link between the bracket and the distal end of the pocket comprise an inextensible sheet connecting said two members over the entire length.

6. A blood pump according to claim 1, wherein the drive means comprise an electric motor whose outer stator body is fixed to the drum and whose rotor drives the bracket.

7. A blood pump according to claim 6, further including means for determining the relative angular position of the bracket relative to the drum, and cooperating with means for interrupting the power supply to the drive means when a predetermined angular value is reached.

8. A blood pump according to claim 7, wherein the electric motor is a reversible motor which is supplied with reverse voltage at reduced value once a predetermined angular position is reached to assist the return of the pump components to their starting position.

9. A blood pump according to claim 8, wherein the reverse voltage at reduced value is variable in such a manner as to adjust the duration of the return phase as a function of reference data concerning the frequency of operation.

10. A blood pump according to claim 1, comprising two closed pockets each having its own inlet valve and its own outlet valve, said pocket being adjacent to each other inside the shell and having their respective proximal ends connected together to the drum and their respective distal ends connected together to the bracket by a common traction link, the pocket which is directly compressed by contact with the drum forming the left ventricle, and the other pocket which is indirectly compressed by virtue of the interposed first pocket, constituting the right ventricle.

* * * * *

UNITED STATES PATENT AND TRADEMARK OFFICE
CERTIFICATE OF CORRECTION

PATENT NO. : 4,576,606

DATED : Mar. 18, 1986

INVENTOR(S) : Pol et al.

It is certified that error appears in the above-identified patent and that said Letters Patent is hereby corrected as shown below:

On the title page after the assignee, "Clinique de la Residence du Parc, insert -- Part interest --.

Signed and Sealed this

Fourteenth Day of October, 1986

[SEAL]

*Attest:*

DONALD J. QUIGG

*Attesting Officer*  *Commissioner of Patents and Trademarks*